United States Patent
Schwarzrock et al.

(10) Patent No.: US 11,826,478 B2
(45) Date of Patent: Nov. 28, 2023

(54) TRANSDERMAL DELIVERY FORMULATION

(71) Applicant: TRS II, LLC, Minneapolis, MN (US)

(72) Inventors: Ted Schwarzrock, Minneapolis, MN (US); Gary Cleary, Los Altos Hills, CA (US)

(73) Assignee: TRS II, LLC, Minneapolis, MN (US)

( * ) Notice: Subject to any disclaimer, the term of this patent is extended or adjusted under 35 U.S.C. 154(b) by 19 days.

(21) Appl. No.: 17/174,947

(22) Filed: Feb. 12, 2021

(65) Prior Publication Data

US 2021/0338599 A1 Nov. 4, 2021

Related U.S. Application Data

(63) Continuation of application No. 15/736,651, filed as application No. PCT/US2016/037437 on Jun. 14, 2016, now abandoned.

(60) Provisional application No. 62/175,363, filed on Jun. 14, 2015.

(51) Int. Cl.
| | |
|---|---|
| *A61K 31/593* | (2006.01) |
| *A61K 47/10* | (2017.01) |
| *A61K 47/14* | (2017.01) |
| *A61K 9/70* | (2006.01) |
| *A61K 31/592* | (2006.01) |
| *A61K 31/59* | (2006.01) |

(52) U.S. Cl.
CPC .......... *A61K 9/7061* (2013.01); *A61K 9/7046* (2013.01); *A61K 9/7069* (2013.01); *A61K 31/59* (2013.01); *A61K 31/592* (2013.01); *A61K 31/593* (2013.01); *A61K 47/10* (2013.01); *A61K 47/14* (2013.01)

(58) Field of Classification Search
None
See application file for complete search history.

(56) References Cited

U.S. PATENT DOCUMENTS

| | | | |
|---|---|---|---|
| 6,024,976 | A | 2/2000 | Miranda et al. |
| 6,538,039 | B2 | 3/2003 | Laurent |
| 6,562,370 | B2 | 5/2003 | Luo et al. |
| 6,565,879 | B1 | 5/2003 | Luo et al. |

(Continued)

FOREIGN PATENT DOCUMENTS

| | | |
|---|---|---|
| JP | 2013119528 A | 6/2013 |
| WO | 2004028515 A1 | 4/2004 |

OTHER PUBLICATIONS

International Search Report and Written Opinion of the ISA/US dated Sep. 16, 2016 in International Application No. PCT/US2016/037437; 19pgs.

(Continued)

*Primary Examiner* — Lakshmi S Channavajjala
(74) *Attorney, Agent, or Firm* — Haukaas Fortius PLLC; Michael Haukaas

(57) ABSTRACT

The invention provides compositions and methods for delivering vitamin D to a human subject. In one embodiment the invention provides a transdermal patch for the transdermal administration of vitamin D comprising: (a) a backing layer that serves as the outer surface of the patch during use; (b) an adhesive drug reservoir layer for affixing the patch to human skin; and (c) a release liner, which upon removal exposes the adhesive drug reservoir layer. The adhesive drug reservoir layer can include vitamin D, a polymeric adhesive, an organic solvent, and a permeation enhancer.

21 Claims, 3 Drawing Sheets

Summary: Cholecalciferol Permeation from Formulations without Adhesives

(56) References Cited

U.S. PATENT DOCUMENTS

| | | |
|---|---|---|
| 6,569,449 B1 | 5/2003 | Stinchcomb et al. |
| 6,570,054 B1 | 5/2003 | Gatto et al. |
| 6,582,724 B2 | 6/2003 | Hsu et al. |
| 6,586,000 B2 | 7/2003 | Luo et al. |
| 6,645,520 B2 | 11/2003 | Hsu et al. |
| 6,719,997 B2 | 4/2004 | Hsu et al. |
| 6,835,392 B2 | 12/2004 | Hsu et al. |
| 6,943,197 B2 | 9/2005 | Maibach et al. |
| 7,205,003 B2 | 4/2007 | Maibach et al. |
| 7,244,447 B2 | 7/2007 | Hsu et al. |
| 8,207,149 B2 | 6/2012 | Tabash et al. |
| 2003/0109506 A1 | 6/2003 | Hayes et al. |
| 2012/0220962 A1 | 8/2012 | Hsu et al. |
| 2013/0143845 A1 | 6/2013 | Supple et al. |

OTHER PUBLICATIONS

Kennel et al., "Vitamin D Deficiency in Adults: When to Test and How to Treat," Mayo Clin Proc., 85(8):752-758, Aug. 2010.

With isosorbide dimethyl ether:

With isopropyl laurate:

TRANSDERMAL DELIVERY FORMULATION

RELATED APPLICATIONS

This application is a continuation of U.S. patent application Ser. No. 15/736,651 filed Dec. 14, 2017, which is a National Stage filing under 35 U.S.C. § 371 of International Application No. PCT/US2016/037437 filed Jun. 14, 2016, which claims priority under 35 U.S.C. § 119(e) to U.S. Provisional Patent Application No. 62/175,363, filed Jun. 14, 2015, which applications are incorporated herein by reference.

BACKGROUND OF THE INVENTION

The delivery of drugs through the skin provides many advantages; primarily, such a means of delivery is a comfortable, convenient and noninvasive way of administering drugs. The variable rates of absorption and metabolism encountered in oral treatment are avoided, and other inherent inconveniences, e.g., gastrointestinal irritation and the like, are eliminated as well. Transdermal drug delivery also makes possible a high degree of control over blood concentrations of any particular drug.

Skin is a structurally complex, relatively thick membrane. Molecules moving from the environment into and through intact skin must first penetrate the stratum corneum and any material on its surface. They must then penetrate the viable epidermis, the papillary dermis, and the capillary walls into the blood stream or lymph channels. To be so absorbed, molecules must overcome a different resistance to penetration in each type of tissue. Transport across the skin membrane is thus a complex phenomenon. However, it is the cells of the stratum corneum, which present the primary barrier to absorption of topical compositions or transdermally administered drugs. The stratum corneum is a thin layer of dense, highly keratinized cells approximately 10-15 microns thick over most of the body. It is believed to be the high degree of keratinization within these cells as well as their dense packing which creates in most cases a substantially impermeable barrier to drug penetration. With many drugs, the rate of permeation through the skin is extremely low without the use of some means to enhance the permeability of the skin.

Numerous chemical agents have been studied as a means of increasing the rate at which a drug penetrates through the skin. As will be appreciated by those in the field, chemical enhancers are compounds that are administered along with the drug (or in some cases the skin may be pretreated with a chemical enhancer) in order to increase the permeability of the stratum corneum, and thereby provide for enhanced penetration of the drug through the skin. Ideally, such chemical penetration enhancers or "permeation enhancers," as the compounds are referred to herein, are compounds that are innocuous and serve merely to facilitate diffusion of the drug through the stratum corneum. The permeability of many therapeutic agents with diverse physicochemical characteristics may be enhanced using these chemical enhancement means. However, there are skin irritation and sensitization problems associated with high levels of certain enhancers.

Accordingly, although there are many chemical methods of enhancing permeation, there remains an ongoing need for a method that is highly effective in increasing the rate at which a drug permeates the skin, does not result in skin damage, irritation, sensitization, or the like, and can be used to effect transdermal delivery of fat-soluble compounds such as vitamin D. It has now been discovered that the formulation described herein is highly effective and provides all of the aforementioned advantages relative to known permeation enhancers.

SUMMARY

The invention provides a transdermal patch for the transdermal administration of vitamin D comprising: (a) a backing layer that serves as the outer surface of the patch during use; (b) an adhesive drug reservoir layer for affixing the patch to human skin; and (c) a release liner, which upon removal exposes the adhesive drug reservoir layer. The adhesive drug reservoir layer can include, or can consist only of, vitamin D, a polymeric adhesive, an organic solvent, and a permeation enhancer.

In one embodiment, the vitamin D is cholecalciferol (vitamin $D_3$), calcifediol (25-hydroxyvitamin $D_3$), ergocalciferol (vitamin DA calcitriol, or calcipotriene. In one embodiment, the adhesive is a polyisobutylene adhesive, a silicone adhesive; or an acrylate adhesive.

In one embodiment, the adhesive drug reservoir layer comprises about 1-10 wt. % of the vitamin D. In one embodiment, the adhesive drug reservoir layer comprises about 60-90 wt. % of the polymeric adhesive. In one embodiment, the adhesive drug reservoir layer comprises about 1-15 wt. % of the organic solvent. In one embodiment, the adhesive drug reservoir layer comprises about 1-15 wt. % of the permeation enhancer. In one specific embodiment, the vitamin D is cholecalciferol, the adhesive is an acrylate adhesive, the organic solvent is ethanol, and the permeation enhancer is transcutol. In other specific embodiments, the organic solvent is isosorbide dimethyl ether, isopropyl laurate, or methyl laurate.

In some embodiments, the adhesive drug reservoir layer does not contain water. In various embodiments, the adhesive drug reservoir layer does not contain an organic base or an inorganic base.

In certain embodiments, the surface area of the adhesive drug reservoir layer of the patch is about 30 $cm^2$ to about 50 $cm^2$. In various embodiments, the patch is formulated to deliver greater than 2,000 µg of vitamin D through 40 $cm^2$ of intact unbroken living skin in within 5 hours. In some embodiments, the patch is formulated to deliver greater than 20,000 µg of vitamin D through 40 $cm^2$ of intact unbroken living skin in within 24 hours. In some embodiments, the patch is formulated to contain about 2,000 to about 300,000 I.U. of vitamin D. In other embodiments, the patch is formulated to contain about 4,000 to about 50,000 I.U. of vitamin D. In certain embodiments, the patch is formulated to contain about 4,000 to about 10,000 I.U. of vitamin D. In certain other embodiments, the patch is formulated to contain about 4,000 to about 5,000 I.U. of vitamin D. In one embodiments, the patch is formulated to contain about 4,000 I.U. of vitamin D.

The invention also provides a transdermal patch for the transdermal administration of vitamin $D_3$ consisting of: (a) a backing layer that serves as the outer surface of the patch during use; (b) an adhesive drug reservoir layer for affixing the patch to human skin; and (c) a release liner, which upon removal exposes the adhesive drug reservoir layer; wherein the adhesive drug reservoir layer consists of 1-10 wt. % of vitamin $D_3$, 60-90 wt. % of a polymeric adhesive, an organic solvent, and 1-15 wt. % of transcutol. The adhesive drug reservoir layer can consist of about 3 wt. % of vitamin $D_3$, 80-85 wt. % of a polymeric adhesive, an organic solvent, and 5-10 wt. % of transcutol.

The invention further provides a method for the transdermal delivery of vitamin D comprising removing the release liner of a transdermal patch described herein and applying the transdermal patch to intact unbroken living skin of a human subject, wherein the transdermal patch delivers greater than 0.75 µg/cm$^2$ of vitamin D to the subject within 5 hours, or at least 10 µg/cm$^2$ of vitamin D to the subject within 48 hours (see FIGS. 3 and 4).

The transdermal patch can be applied to a subject having a 25-hydroxyvitamin $D_3$ blood serum level of less than 30 ng/mL. The transdermal patch can be applied to a subject having a 25-hydroxyvitamin $D_3$ blood serum level of about 1 ng/mL to about 25 ng/mL. In some embodiments, the 25-hydroxyvitamin $D_3$ blood serum level of the subject increases to greater than 30 ng/mL within 5 hours. In various embodiments, the transdermal patch is applied to the subject once per day for at least 5 days. In one specific embodiment, the human subject has a 25-hydroxyvitamin $D_3$ blood serum level of less than 20 ng/mL. In another specific embodiment, the human subject has cystic fibrosis, is older than 65 years of age, has undergone bariatric surgery, or a combination thereof.

The invention also provides a method of increasing the 25-hydroxyvitamin $D_3$ blood serum level of a human subject that has a vitamin D malabsorption condition comprising removing the release liner of the transdermal patch described herein and applying the transdermal patch to intact unbroken living skin of the human subject, wherein the 25-hydroxyvitamin $D_3$ blood serum level of the subject increases to greater than 20 ng/mL within 24 hours. The human subject that can have a vitamin D malabsorption condition is a subject that has been diagnosed with cystic fibrosis.

The invention therefore provides for the use of the compositions described herein for use in medical therapy. The medical therapy can be treating cystic fibrosis and symptoms associated therewith. The invention also provides for the use of a composition as described herein for the manufacture of a medicament to treat an adverse health condition in a mammal, for example, a vitamin D deficiency in a human. The medicament can include a pharmaceutically acceptable diluent, excipient, or carrier, and can be delivered by an occlusive transdermal patch.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Figure 1:
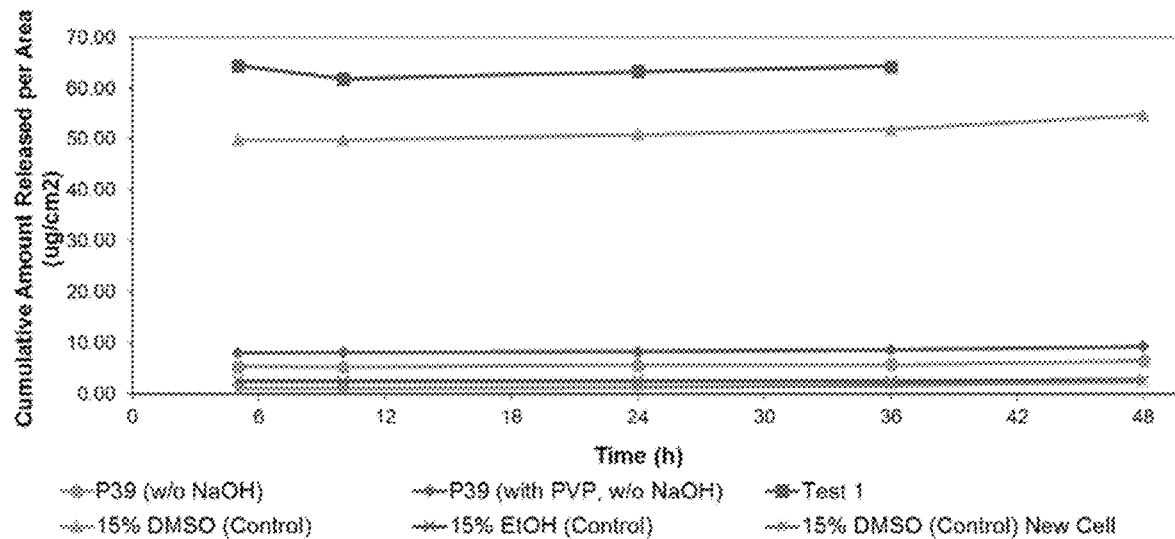
FIG. 1. Summary graph of cholecalciferol permeation from formulations without adhesives showing data collected from 5 hours to 36 hours post-application.

The compositions and methods described herein can involves the use of a drug delivery system, e.g., a topical or transdermal "patch," wherein the active agent is contained within a laminated structure that is to be affixed to the skin. In such a structure, the drug composition is contained in a layer, or "reservoir," underlying an upper backing layer that serves as the outer surface of the device during use. The laminated structure may contain a single reservoir, or it may contain multiple reservoirs.

Accordingly, another embodiment of the invention is a system for the enhanced topical or transdermal administration of a drug, comprising: (a) at least one drug reservoir containing the drug and a pharmaceutically acceptable carrier; (b) a means for maintaining the system in drug and base transmitting relationship to the body surface and forming a body surface-system interface; and (c) a backing layer that serves as the outer surface of the device during use.

In one embodiment, the drug reservoir comprises a polymeric matrix of a pharmaceutically acceptable adhesive material that serves to affix the system to the skin during drug delivery; typically, the adhesive material is a pressure-sensitive adhesive (PSA) that is suitable for long-term skin contact, and which should be physically and chemically compatible with the active agent, inorganic or organic base, and any carriers, vehicles or other additives that are present. Examples of suitable adhesive materials include, but are not limited to, the following: polyethylenes; polysiloxanes; polyisobutylenes; polyacrylates; polyacrylamides; polyurethanes; plasticized ethylene-vinyl acetate copolymers; and tacky rubbers such as polyisobutene, polybutadiene, polystyrene-isoprene copolymers, polystyrene-butadiene copolymers, and neoprene (polychloroprene). One specific adhesive is polyisobutylene.

The backing layer functions as the primary structural element of the transdermal system and provides the device with flexibility and, preferably, occlusivity. The material used for the backing layer should be inert and incapable of absorbing the drug, the base enhancer, or other components of the formulation contained within the device. The backing is preferably comprised of a flexible elastomeric material that serves as a protective covering to prevent loss of drug and/or vehicle via transmission through the upper surface of the patch, and will preferably impart a degree of occlusivity to the system, such that the area of the body surface covered by the patch becomes hydrated during use. The material used for the backing layer should permit the device to follow the contours of the skin and be worn comfortably on areas of skin such as at joints or other points of flexure, that are normally subjected to mechanical strain with little or no likelihood of the device disengaging from the skin due to differences in the flexibility or resiliency of the skin and the device. The materials used as the backing layer are either occlusive or permeable, as noted above, although occlusive backings are preferred, and are generally derived from synthetic polymers (e.g., polyester, polyethylene, polypropylene, polyurethane, polyvinylidine chloride, and polyether amide), natural polymers (e.g., cellulosic materials), or macroporous woven and nonwoven materials.

During storage and prior to use, the laminated structure preferably includes a release liner. Immediately prior to use, this layer is removed from the device so that the system may be affixed to the skin. The release liner should be made from a drug/vehicle impermeable material, and is a disposable element, which serves only to protect the device prior to application. Typically, the release liner is formed from a material impermeable to the pharmacologically active agent and the base enhancer, and is easily stripped from the transdermal patch prior to use.

In an alternative embodiment, the drug-containing reservoir and skin contact adhesive are present as separate and distinct layers, with the adhesive underlying the reservoir. In such a case, the reservoir may be a polymeric matrix as described above. Alternatively, the reservoir may be comprised of a liquid or semisolid formulation contained in a closed compartment or pouch, or it may be a hydrogel reservoir, or may take some other form. Hydrogel reservoirs are particularly preferred herein. As will be appreciated by those skilled in the art, hydrogels are macromolecular networks that absorb water and thus swell but do not dissolve in water. That is, hydrogels contain hydrophilic functional groups that provide for water absorption, but the hydrogels are comprised of crosslinked polymers that give rise to aqueous insolubility. Generally, then, hydrogels are comprised of crosslinked hydrophilic polymers such as a polyurethane, a polyvinyl alcohol, a polyacrylic acid, a polyoxyethylene, a polyvinylpyrrolidone, a poly(hydroxyethyl methacrylate) (poly(HEMA)), or a copolymer or mixture thereof. Particularly preferred hydrophilic polymers are copolymers of HEMA and polyvinylpyrrolidone.

Additional layers, e.g., intermediate fabric layers and/or rate-controlling membranes, may also be present in any of these drug delivery systems. Fabric layers may be used to facilitate fabrication of the device, while a rate-controlling membrane may be used to control the rate at which a component permeates out of the device. The component may be a drug, a base enhancer, an additional enhancer, or some other component contained in the drug delivery system.

A rate-controlling membrane, if present, will be included in the system on the skin side of one or more of the drug reservoirs. The material used to form such a membrane is selected so as to limit the flux of one or more components contained in the drug formulation. Representative materials useful for forming rate-controlling membranes include polyolefins such as polyethylene and polypropylene, polyamides, polyesters, ethylene-ethacrylate copolymer, ethylene-vinyl acetate copolymer, ethylene-vinyl methylacetate copolymer, ethylene-vinyl ethylacetate copolymer, ethylene-vinyl propylacetate copolymer, polyisoprene, polyacrylonitrile, ethylene-propylene copolymer, and the like.

Generally, the underlying surface of the transdermal device, i.e., the skin contact area, has an area in the range of about 5-200 $cm^2$, preferably 5-100 $cm^2$, more preferably 20-60 $cm^2$. That area will vary, of course, with the amount of drug to be delivered and the flux of the drug through the body surface. Larger patches can be used to accommodate larger quantities of drug, while smaller patches can be used for smaller quantities of drug and/or drugs that exhibit a relatively high permeation rate.

Such drug delivery systems may be fabricated using conventional coating and laminating techniques known in the art. For example, adhesive matrix systems can be prepared by casting a fluid admixture of adhesive, drug and vehicle onto the backing layer, followed by lamination of the release liner. Similarly, the adhesive mixture may be cast onto the release liner, followed by lamination of the backing layer. Alternatively, the drug reservoir may be prepared in the absence of drug or excipient, and then loaded by soaking in a drug/vehicle mixture. In general, transdermal systems of the invention are fabricated by solvent evaporation, film casting, melt extrusion, thin film lamination, die cutting, or the like. The inorganic or organic base permeation enhancer will generally be incorporated into the device during patch manufacture rather than subsequent to preparation of the device. Thus, for acid addition salts of basic drugs (e.g., hydrochloride salts of amine drugs), the enhancer will neutralize the drug during manufacture of the drug delivery system, resulting in a final drug delivery system in which the drug is present in nonionized, neutral form along with an excess of base to serve as a permeation enhancer. For nonionized acidic drugs, the base will neutralize such drugs by converting them to the ionized drug in salt form.

In a preferred delivery system, an adhesive overlayer that also serves as a backing for the delivery system is used to better secure the patch to the body surface. This overlayer is sized such that it extends beyond the drug reservoir so that adhesive on the overlayer comes into contact with the body surface. The overlayer is useful because the adhesive/drug reservoir layer may lose its adhesion a few hours after application due to hydration. By incorporating an adhesive overlayer, the delivery system will remain in place for the required period of time.

Other types and configurations of transdermal drug delivery systems may also be used in conjunction with the method of the present invention, as will be appreciated by those skilled in the art of transdermal drug delivery. See, for example, Ghosh, Transdermal and Topical Drug Delivery Systems (Interpharm Press, 1997), particularly Chapters 2 and 8.

As with the topically applied formulations of the invention, the drug and enhancer composition contained within the drug reservoir(s) of these laminated systems may comprise a number of additional components. In some cases, the drug and enhancer may be delivered neat, i.e., in the absence of additional liquid. In most cases, however, the drug will be dissolved, dispersed or suspended in a suitable pharmaceutically acceptable vehicle, typically a solvent or gel. Other components that may be present include preservatives, stabilizers, surfactants, solubilizers, additional enhancers, and the like.

The invention accordingly provides a novel and highly effective means for increasing the flux of an active agent through the body surface (skin or mucosal tissue) of a human or animal. The base enhancers discussed herein, employed in specific amounts relative to a formulation or drug reservoir, may be used as permeation enhancers with a wide variety of drugs and drug types, including free acids, free bases, acid addition salts of basic drugs, basic addition salts of acidic drugs, nonionizable drugs, peptides and proteins. Surprisingly, the increase in permeation is not accompanied by any noticeable tissue damage, irritation, or sensitization. The invention thus represents an important advance in the field of drug delivery.

It is to be understood that while the invention has been described in conjunction with the preferred specific embodiments thereof, the foregoing description is intended to illustrate and not limit the scope of the invention. Other aspects, advantages and modifications will be apparent to those skilled in the art to which the invention pertains. Furthermore, the practice of the present invention will employ, unless otherwise indicated, conventional techniques of drug formulation, particularly topical and transdermal drug formulation, which are within the skill of the art. Such techniques are fully explained in the literature. See *Remington: The Science and Practice of Pharmacy*, cited supra, as well as Goodman & Gilman's The Pharmacological Basis of Therapeutics, 10$^{th}$ Ed. (2001). Techniques that can be used for the preparation of transdermal patches and the analysis thereof are further described by U.S. Patent Publication No. 2012/0220962.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, the composition, or the embodiment. The term about can also modify the end-points of a recited range as discuss above in this paragraph.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a disease, disorder, and/or condition, or to bring about a recited effect. For example, an effective amount can be an amount effective to reduce the progression or severity of the condition or symptoms being treated. Determination of a therapeutically effective amount is well within the capacity of persons skilled in the art. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect.

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can extend to prophylaxis and can include prevent, prevention, preventing, lowering, stopping or reversing the progression or severity of the condition or symptoms being treated. As such, the term "treatment" can include medical, therapeutic, and/or prophylactic administration, as appropriate.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

"Body surface" is used to refer to skin or mucosal tissue.

"Carriers" or "vehicles" as used herein refer to carrier materials suitable for transdermal or topical drug administration. Carriers and vehicles useful herein include any such materials known in the art, which are nontoxic and do not interact with other components of the composition in a deleterious manner.

"Penetration enhancement" or "permeation enhancement" as used herein relates to an increase in the permeability of the skin or mucosal tissue to the selected pharmacologically active agent, i.e., so that the rate at which the agent permeates therethrough (i.e., the "flux" of the agent through the body surface) is increased relative to the rate that would be obtained in the absence of permeation enhancer. The enhanced permeation effected through the use of such enhancers can be observed by measuring the rate of diffusion of drug through animal or human skin using, for example a Franz diffusion apparatus as known in the art and as employed in the Examples herein.

"Predetermined area" of skin or mucosal tissue refers to the area of skin or mucosal tissue through which a drug-enhancer formulation is delivered, and is a defined area of intact unbroken living skin or mucosal tissue. That area will usually be in the range of about 5-200 cm$^2$, more usually in the range of about 5-100 cm$^2$, preferably in the range of about 20-60 cm$^2$. However, it will be appreciated by those skilled in the art of drug delivery that the area of skin or mucosal tissue through which drug is administered may vary significantly, depending on patch configuration, dose, and the like.

"Topical administration" is used in its conventional sense to mean delivery of a topical drug or pharmacologically active agent to the skin or mucosa, as in, for example, the treatment of various skin disorders. Topical administration, in contrast to transdermal administration, provides a local rather than a systemic effect. However, unless otherwise stated or implied, the terms "topical drug administration" and "transdermal drug administration" are used interchangeably.

"Transdermal" drug delivery is meant administration of a drug to the skin surface of an individual so that the drug passes through the skin tissue and into the individual's blood stream, thereby providing a systemic effect. The term "transdermal" is intended to include "transmucosal" drug administration, i.e., administration of a drug to the mucosal (e.g., sublingual, buccal, vaginal, rectal) surface of an individual so that the drug passes through the mucosal tissue and into the individual's blood stream.

Drug Reservoir Components and Variations

The components of the drug reservoir can be aqueous or non-aqueous. The reservoir can include a topical formulation such as a gel, ointment, lotion, or other topical formulation, typically in combination with an adhesive. Accordingly, while the method of delivery of the active agent may vary, the method will typically involve application of a formulation or drug delivery system containing a pharmaceutically acceptable carrier to a predetermined area of the skin or other tissue for a period of time sufficient to provide the desired local or systemic effect. The method may involve direct application of the composition as an ointment, gel, cream, or the like, or may involve use of a drug delivery device such as a patch. In either case, water can be present in order for ions to be provided and thus enhance the flux of the active agent through the patient's body surface. Thus, such a formulation or drug reservoir may be aqueous, i.e., contain water, or may be nonaqueous and used in combination with an occlusive backing layer so that moisture evaporating from the body surface is maintained within the formulation or transdermal system during drug administration. In some cases, however, e.g., with an occlusive gel, a nonaqueous formulation may be used with or without an occlusive backing layer.

Suitable formulations include ointments, creams, gels, lotions, solutions, pastes, and the like. Ointments, as is well known in the art of pharmaceutical formulation, are semisolid preparations that are typically based on petrolatum or other petroleum derivatives. The specific ointment foundation to be used, as will be appreciated by those skilled in the art, is one that will provide for optimum drug delivery, and, preferably, will provide for other desired characteristics as well, e.g., emolliency or the like. As with other carriers or vehicles, the ointment foundation should be inert, stable, nonirritating and nonsensitizing. As explained in Remington: *The Science and Practice of Pharmacy*, 22$^{th}$ edition (Lippincott Williams & Wilkins, 2000), ointment foundations may be grouped in four classes: oleaginous, emulsifiable, emulsion, and water-soluble. Oleaginous ointment foundations include, for example, vegetable oils, fats obtained from animals, and semisolid hydrocarbons obtained from petroleum. Emulsifiable ointment foundations, also known as absorbent ointment foundations, contain little or no water and include, for example, hydroxystearin sulfate, anhydrous lanolin and hydrophilic petrolatum. Emulsion ointment foundations are either water-in-oil (W/O) emulsions or oil-in-water (O/W) emulsions, and include, for example, cetyl alcohol, glyceryl monostearate, lanolin and stearic acid. Preferred water-soluble ointment foundations are prepared from polyethylene glycols of varying molecular weight.

Creams, as also well known in the art, are viscous liquids or semisolid emulsions, either oil-in-water or water-in-oil. Cream foundations are water-washable, and contain an oil phase, an emulsifier and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic or amphoteric surfactant.

As will be appreciated by those working in the field of pharmaceutical formulation, gels are semisolid, suspension-type systems. Single-phase gels contain organic macromolecules distributed substantially uniformly throughout the carrier liquid, which is typically aqueous, but also may contain an alcohol and, optionally, an oil. Preferred organic macromolecules, i.e., gelling agents, are crosslinked acrylic acid polymers such as the "carbomer" family of polymers, e.g., carboxypolyalkylenes that may be obtained commercially under the Carbopol® trademark. Also preferred are hydrophilic polymers such as polyethylene oxides, polyoxyethylene-polyoxypropylene copolymers and polyvinylalcohol; cellulosic polymers such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof.

Lotions, which are preferred for delivery of cosmetic agents, are preparations to be applied to the skin surface without friction, and are typically liquid or semiliquid preparations in which solid particles, including the active agent, are present in a water or alcohol base. Lotions are usually suspensions of solids, and preferably, for the present purpose, comprise a liquid oily emulsion of the oil-in-water type. Lotions are preferred formulations herein for treating large body areas, because of the ease of applying a more fluid composition. It is generally necessary that the insoluble matter in a lotion be finely divided. Lotions will typically contain suspending agents to produce better dispersions as well as compounds useful for localizing and holding the active agent in contact with the skin, e.g., methylcellulose, sodium carboxymethyl-cellulose, or the like.

Solutions are homogeneous mixtures prepared by dissolving one or more chemical substances (solute) in another liquid such that the molecules of the dissolved substance are dispersed among those of the solvent. The solution may contain other pharmaceutically acceptable chemicals to buffer, stabilize or preserve the solute. Commonly used examples of solvents used in preparing solutions are ethanol, water, propylene glycol or any other pharmaceutically acceptable vehicle.

Pastes are semisolid dosage forms in which the active agent is suspended in a suitable foundation. Depending on the nature of the foundation, pastes are divided between fatty pastes or those made from single-phase, aqueous gels. The foundation in a fatty paste is generally petrolatum or hydrophilic petrolatum or the like. The pastes made from single-phase aqueous gels generally incorporate carboxymethylcellulose or the like as the foundation.

Formulations may also be prepared with liposomes, micelles, and microspheres. Liposomes are microscopic vesicles having a lipid wall comprising a lipid bilayer, and can be used as drug delivery systems herein as well. Generally, liposome formulations are preferred for poorly soluble or insoluble pharmaceutical agents. Liposomal preparations for use in the instant invention include cationic (positively charged), anionic (negatively charged) and neutral preparations. Cationic liposomes are readily available. For example, N-[1-2,3-dioleyloxy)propyl]-N,N,N-triethylammonium liposomes are available under the tradename Lipofectin® (GIBCO BRL, Grand Island, N.Y.). Anionic and neutral liposomes are readily available as well, e.g., from Avanti Polar Lipids (Birmingham, Ala.), or can be easily prepared using readily available materials. Such materials include phosphatidyl choline, cholesterol, phosphatidyl ethanolamine, dioleoylphosphatidyl choline, dioleoylphosphatidyl glycerol, dioleoylphoshatidyl ethanolamine, among others. These materials can also be mixed with N-[1-2,3-dioleyloxy)propyl]-N,N,N-triethylammonium (DOTMA) in appropriate ratios. Methods for making liposomes using these materials are well known in the art.

Micelles are known in the art and are comprised of surfactant molecules arranged so that their polar headgroups form an outer spherical shell, while the hydrophobic, hydrocarbon chains are oriented towards the center of the sphere, forming a core. Micelles form in an aqueous solution containing surfactant at a high enough concentration so that micelles naturally result. Surfactants useful for forming micelles include, but are not limited to, potassium laurate, sodium octane sulfonate, sodium decane sulfonate, sodium dodecane sulfonate, sodium lauryl sulfate, docusate sodium, decyltrimethylammonium bromide, dodecyltrimethylammonium bromide, tetradecyltrimethylammonium bromide, tetradecyltrimethyl-ammonium chloride, dodecylammonium chloride, polyoxyl 8 dodecyl ether, polyoxyl 12 dodecyl ether, nonoxynol 10 and nonoxynol 30. Micelle formulations can be used in conjunction with the present invention either by incorporation into the reservoir of a topical or transdermal delivery system, or into a formulation to be applied to the body surface.

Microspheres, similarly, may be incorporated into the present formulations and drug delivery systems. Like liposomes and micelles, microspheres essentially encapsulate a drug or drug-containing formulation. They are generally, although not necessarily, formed from lipids, preferably charged lipids such as phospholipids. Preparation of lipidic microspheres is well known in the art and described in the pertinent texts and literature.

Various additives, known to those skilled in the art, may be included in the topical formulations. For example, solvents, including relatively small amounts of alcohol, may be used to solubilize certain drug substances. Other optional additives include opacifiers, antioxidants, fragrance, colorant, gelling agents, thickening agents, stabilizers, surfactants and the like. Other agents may also be added, such as antimicrobial agents, to prevent spoilage upon storage, i.e., to inhibit growth of microbes such as yeasts and molds. Suitable antimicrobial agents are typically selected from the group consisting of the methyl and propyl esters of p-hydroxybenzoic acid (i.e., methyl and propyl paraben), sodium benzoate, sorbic acid, imidurea, and combinations thereof.

For those drugs having an unusually low rate of permeation through the skin or mucosal tissue, it may be desirable to include a second permeation enhancer in the formulation in addition to the inorganic or organic base enhancer, although in a preferred embodiment the base enhancer is administered without any other permeation enhancers. Any other enhancers should, like the base enhancer, minimize the possibility of skin damage, irritation, and systemic toxicity. Examples of classes of suitable secondary enhancers (or "co-enhancers") include, but are not limited to, fatty acids, both saturated and unsaturated; fatty alcohols; bile acids; nonionic surfactants, including esters of fatty acids, fatty (long-chain alkyl or alkenyl) esters of monohydric alcohols, diols, and polyols, diols and polyols that are both esterified with a fatty acid and substituted with a polyoxyalkylene, polyoxyalkylene fatty acid esters, polyoxyalkylene fatty ethers, polyoxyalkylene fatty ethers, and polyglyceryl fatty acid esters; amines; amides; N-alkyl-azacycloalkanones and N-alkyl-azacycloalkenones; hydrocarbon solvents; terpenes;

lower alkyl esters; cyclodextrin enhancers; nitrogen-containing heterocycles; sulfoxides; and urea and its derivatives.

Specific examples of suitable co-enhancers include ethers such as diethylene glycol monoethyl ether (available commercially as Transcutol® solvent, Gattefosse SA) and diethylene glycol monomethyl ether; surfactants such as sodium laurate, sodium lauryl sulfate, cetyltrimethylammonium bromide, benzalkonium chloride, Poloxamer (231, 182, 184), Tween (20, 40, 60, 80) and lecithin; alcohols such as ethanol, propanol, octanol, benzyl alcohol, and the like; fatty acids such as lauric acid, oleic acid and valeric acid; fatty acid esters such as isopropyl myristate, isopropyl palmitate, methylpropionate, and ethyl oleate; polyols and esters thereof such as polyethylene glycol, and polyethylene glycol monolaurate; amides and other nitrogenous compounds such as urea, dimethylacetamide, dimethylformamide, 2-pyrrolidone, 1-methyl-2-pyrrolidone, ethanolamine, diethanolamine and triethanolamine; terpenes; alkanones; and organic acids, particularly citric acid and succinic acid. Azone® and sulfoxides such as dimethylsulfoxide and decylmethylsulfoxide may also be used, but are less preferred. *Percutaneous Penetration Enhancers*, eds. Smith et al. (CRC Press, 1995) provides an excellent overview of the field and further information concerning possible secondary enhancers for use in conjunction with the present invention.

The formulation may also contain irritation-mitigating additives to minimize or eliminate the possibility of skin irritation or skin damage resulting from the drug, the base enhancer, or other components of the formulation. Suitable irritation-mitigating additives include, for example: α-tocopherol; monoamine oxidase inhibitors, particularly phenyl alcohols such as 2-phenyl-1-ethanol; glycerin; salicylic acids and salicylates; ascorbic acids and ascorbates; ionophores such as monensin; amphiphilic amines; ammonium chloride; N-acetylcysteine; cis-urocanic acid; capsaicin; and chloroquine. The irritant-mitigating additive, if present, may be incorporated into the formulation at a concentration effective to mitigate irritation or skin damage, typically representing not more than about 20 wt %, more typically not more than about 5 wt %, of the formulation.

The concentration of the active agent in the formulation (e.g., vitamin $D_3$) will typically depend upon a variety of factors, including the disease or condition to be treated, the nature and activity of the active agent, the desired effect, possible adverse reactions, the ability and speed of the active agent to reach its intended target, and other factors within the particular knowledge of the patient and physician. Preferred formulations will typically contain on the order of about 0.5-50 wt %, preferably about 2-30 wt %, active agent (i.e., vitamin $D_3$), or about 5-30 wt %, active agent.

In some embodiments, formulation can further include one to three additional vitamin and/or mineral components. One optional component is vitamin $K_2$, which can be present at about 50 μg to about 250 μg per dose, or about 100 μg to about 200 μg per dose. The formulations can also include about 50 mg to about 500 mg of magnesium, about 200 mg to about 300 mg of magnesium, or about 250 mg of magnesium.

Pharmaceutical Formulations

The compounds described herein can be used to prepare therapeutic pharmaceutical compositions, for example, by combining the compounds with a pharmaceutically acceptable diluent, excipient, or carrier. The compounds may be added to a carrier in the form of a salt or solvate. For example, in cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartrate, succinate, benzoate, ascorbate, α-ketoglutarate, and β-glycerophosphate. Suitable inorganic salts may also be formed, including hydrochloride, halide, sulfate, nitrate, bicarbonate, and carbonate salts.

Pharmaceutically acceptable salts may be obtained using standard procedures well known in the art, for example by reacting a sufficiently basic compound such as an amine with a suitable acid to provide a physiologically acceptable ionic compound. Alkali metal (for example, sodium, potassium or lithium) or alkaline earth metal (for example, calcium) salts of carboxylic acids can also be prepared by analogous methods.

The compounds of the formulas described herein can be formulated as pharmaceutical compositions and administered to a mammalian host, such as a human patient, in a variety of forms. The forms can be specifically adapted to a chosen route of administration, e.g., topical, transdermal, or transmucosal routes.

The compounds described herein may be systemically administered in combination with a pharmaceutically acceptable vehicle, such as an inert diluent. The compositions and preparations typically contain at least 0.1% of active compound (i.e., a fat soluble vitamin such as vitamin D). The percentage of the compositions and preparations can vary and may conveniently be from about 0.5% to about 60%, about 1% to about 25%, or about 2% to about 10%, of the weight of a given unit dosage form. The amount of active compound in such therapeutically useful compositions can be such that an effective dosage level can be obtained.

Solutions of the active compound or its salts can be prepared in water or an organic solvent, optionally mixed with a nontoxic surfactant. Dispersions can be prepared in glycerol, liquid polyethylene glycols, triacetin, or mixtures thereof, or in a pharmaceutically acceptable oil. Solutions or dispersions can also be prepared using triglycerides such as triglycerides having a combination of caprylic and capric fatty acids, commercially available as Labrafac Lipophile WL1349 oil. Under ordinary conditions of storage and use, preparations may contain a preservative to prevent the growth of microorganisms.

For topical administration, compounds may be applied in pure form, e.g., when they are liquids. However, it will generally be desirable to administer the active agent to the skin as a composition or formulation, for example, in combination with a dermatologically acceptable carrier, which may be a solid, a liquid, a gel, or the like.

Useful solid carriers include finely divided solids such as talc, clay, microcrystalline cellulose, silica, alumina, and the like. Useful liquid carriers include water, dimethyl sulfoxide (DMSO), alcohols, glycols, or water-alcohol/glycol blends, in which a compound can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using a pump-type or aerosol sprayer, and optionally be covered with an occlusive bandage to enhance absorption.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

Examples of dermatological compositions for delivering active agents to the skin are known to the art; for example, see U.S. Pat. No. 4,992,478 (Geria), U.S. Pat. No. 4,820,508 (Wortzman), U.S. Pat. No. 4,608,392 (Jacquet et al.), and U.S. Pat. No. 4,559,157 (Smith et al.). Such dermatological compositions can be used in combinations with the compounds described herein where an ingredient of such compositions can optionally be replaced by a compound described herein, or a compound described herein can be added to the composition.

Useful dosages of the actives described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of a compound, or an active salt or derivative thereof, required for use in treatment will vary not only with the particular compound or salt selected but also with the route of administration, the nature of the condition being treated, and the age and condition of the patient, and will be ultimately at the discretion of an attendant physician or clinician.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1. Vitamin $D_3$ Transdermal Delivery

Figure 2:
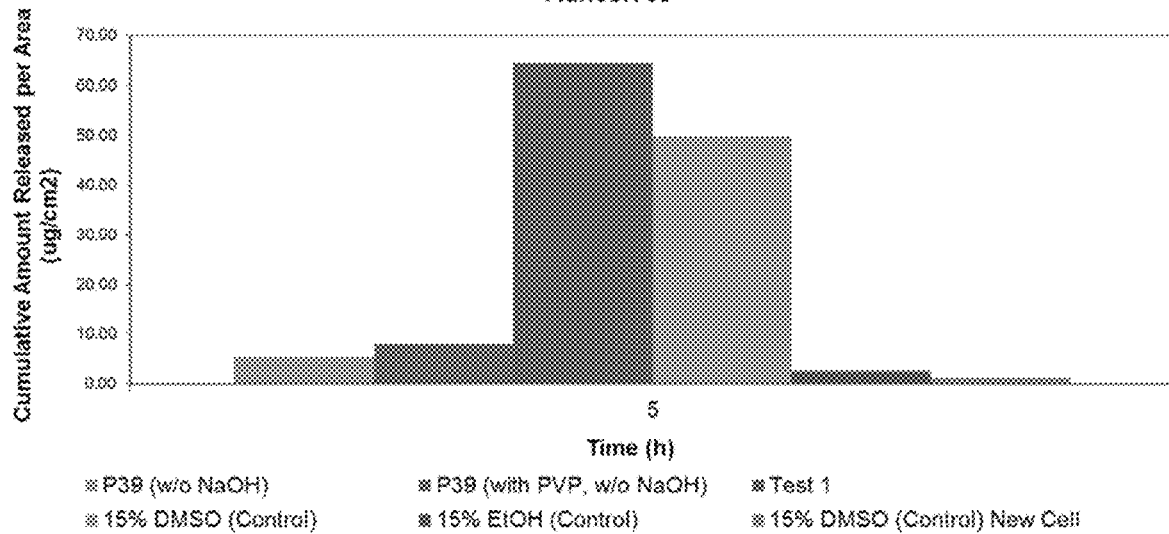
FIG. 2. Summary table of cholecalciferol permeation from formulations without adhesives showing data collected at 5 hours post-application.

Franz cell permeation of vitamin $D_3$ was performed to evaluate various formulations lacking adhesives and the results were analyzed as shown in FIGS. 1 and 2 (transdermal permeation of cholecalciferol through the Franz cells for the P39 formulation (lacking PIB and NaOH) and the Test 1 formulation).

Sample analysis: Permeation samples were analyzed using HPLC with UV detection at 265 nm. A QC standard was prepared using cholecalciferol dissolved in acetonitrile and diluting the same with permeation receiver buffer to obtain a working standard containing about 0.05 mg/mL of cholecalciferol. The second QC standard was prepared as control. The standard was injected was injected five times and the % RSD of these five injections were found to be 0.07. The QC control solution was injected in replicate and the recovery of cholecalciferol was 104.3% when tested against the standard. This comprised the HPLC system suitability before the analysis of the experimental samples. Further during the analysis bracketing standards were injected and their recoveries were calculated against the average of initial five injections to calculate HPLC system drift during the analysis.

Favorable stability results were discovered for P39 formulations that did not contain sodium hydroxide. Accordingly, experiments were performed to confirm that the modified formulations indeed transfer vitamin D through skin. Formulation P39A contains the same components as P39 except that it excludes sodium hydroxide, PIB adhesives, and PVP. Formulation P39B contains the same components as P39 except that it excludes sodium hydroxide and PIB adhesives.

Composition of P39A and B:

| Components: | P39 Quantity (g) | P39A Quantity (g) | P39B Quantity (g) |
|---|---|---|---|
| Cholecalciferol | 0.2 | 0.2 | 0.2 |
| Diethylene glycol mono ethyl ether | 1.0 | 1.0 | 1.0 |
| Sodium lauroyl sarcosinate | 0.1 | 0.1 | 0.1 |
| Poly vinyl pyrrolidine (PVP) | 0.7 | 0 | 0.7 |
| DURO-TAK 87-6908 (PIB) | 15.0 | 0 | 0 |
| Polyisobutylene 926 | 0.5 | 0 | 0 |
| Sodium hydroxide (50% aq.) | 0.3 | 0 | 0 |
| Distilled water | 1.0 | 1.0 | 1.0 |
| Total | 18.8 | 2.3 | 3.0 |
| D3 Concentration approx. | 0.01 g/mL | 0.087 g/mL | 0.067 g/mL |

Composition of Test 1:

| Ingredients: | Quantity (g) |
|---|---|
| Cholecalciferol | 0.2 |
| Ethyl alcohol | 0.5 |
| Transcutol | 1.0 |
| Total | 1.7 |
| D3 Concentration approx. | 0.13 g/mL |

TABLE A

Transdermal Delivery of Cholecalciferol: Results for Permeation from Formulations without Adhesive (FIGS. 1 and 2)

| | | Volume of Receiver Solution Sampled (mL) = 1 | Cross Sectional Area (cm2) = 1.13 | | Cum. Amount |
|---|---|---|---|---|---|
| | Volume of Receiver (mL) = 7.50 | | | Cumulative | Permeated/ |
| S No. | Study: | Time-point (h) | Cholecalciferol found (ug) | Amount Perm. (ug) | Unit Area (ug/cm2) |
| | P39 no adhesive, no NaOH | | | | |
| 1 | Permeation cell-1 5 h | 5 | 6.10 | 6.10 | 5.40 |
| 2 | Permeation cell-1 10 h | 10 | 5.17 | 5.98 | 5.30 |
| 3 | Permeation cell-1 24 h | 24 | 4.85 | 6.46 | 5.72 |
| 4 | Permeation cell-1 36 h | 36 | 4.08 | 6.55 | 5.80 |
| 5 | Permeation cell-1 48 h | 48 | 4.05 | 7.39 | 6.54 |

TABLE A-continued

Transdermal Delivery of Cholecalciferol: Results for Permeation from Formulations without Adhesive (FIGS. 1 and 2)

| S No. | Study: | Volume of Receiver (mL) = 7.50 | Volume of Receiver Solution Sampled (mL) = 1 Time-point (h) | Cross Sectional Area (cm2) = 1.13 Cholecalciferol found (ug) | Cumulative Amount Perm. (ug) | Cum. Amount Permeated/Unit Area (ug/cm2) |
|---|---|---|---|---|---|---|
| | P39 with PVP, no adhesive, no NaOH | | | | | |
| 1 | Permeation cell-2 5 h | | 5 | 9.15 | 9.15 | 8.10 |
| 2 | Permeation cell-2 10 h | | 10 | 8.00 | 9.22 | 8.16 |
| 3 | Permeation cell-2 24 h | | 24 | 6.98 | 9.43 | 8.34 |
| 4 | Permeation cell-2 36 h | | 36 | 6.08 | 9.79 | 8.66 |
| 5 | Permeation cell-2 48 h | | 48 | 5.50 | 10.51 | 9.30 |
| | Test 1, no adhesive | | | | | |
| 1 | Permeation cell-3 5 h | | 5 | 72.83 | 72.83 | 64.45 |
| 2 | Permeation cell-3 10 h | | 10 | 60.15 | 69.86 | 61.82 |
| 3 | Permeation cell-3 24 h | | 24 | 52.56 | 71.59 | 63.35 |
| 4 | Permeation cell-3 36 h | | 36 | 44.12 | 72.69 | 64.33 |
| | 15% DMSO (Control) | | | | | |
| 1 | Permeation cell-4 5 h | | 5 | 56.25 | 56.25 | 49.78 |
| 2 | Permeation cell-4 10 h | | 10 | 48.73 | 56.23 | 49.76 |
| 3 | Permeation cell-4 24 h | | 24 | 42.46 | 57.46 | 50.85 |
| 4 | Permeation cell-4 36 h | | 36 | 35.91 | 58.56 | 51.83 |
| 5 | Permeation cell-4 48 h | | 48 | 31.29 | 61.76 | 54.66 |
| | 15% Ethanol (Control) | | | | | |
| 1 | Permeation cell-5 5 h | | 5 | 2.87 | 2.87 | 2.54 |
| 2 | Permeation cell-5 10 h | | 10 | 2.48 | 2.86 | 2.53 |
| 3 | Permeation cell-5 24 h | | 24 | 2.10 | 2.86 | 2.53 |
| 4 | Permeation cell-5 36 h | | 36 | 1.76 | 2.91 | 2.57 |
| 5 | Permeation cell-5 48 h | | 48 | 1.58 | 3.11 | 2.76 |

Figure 3:
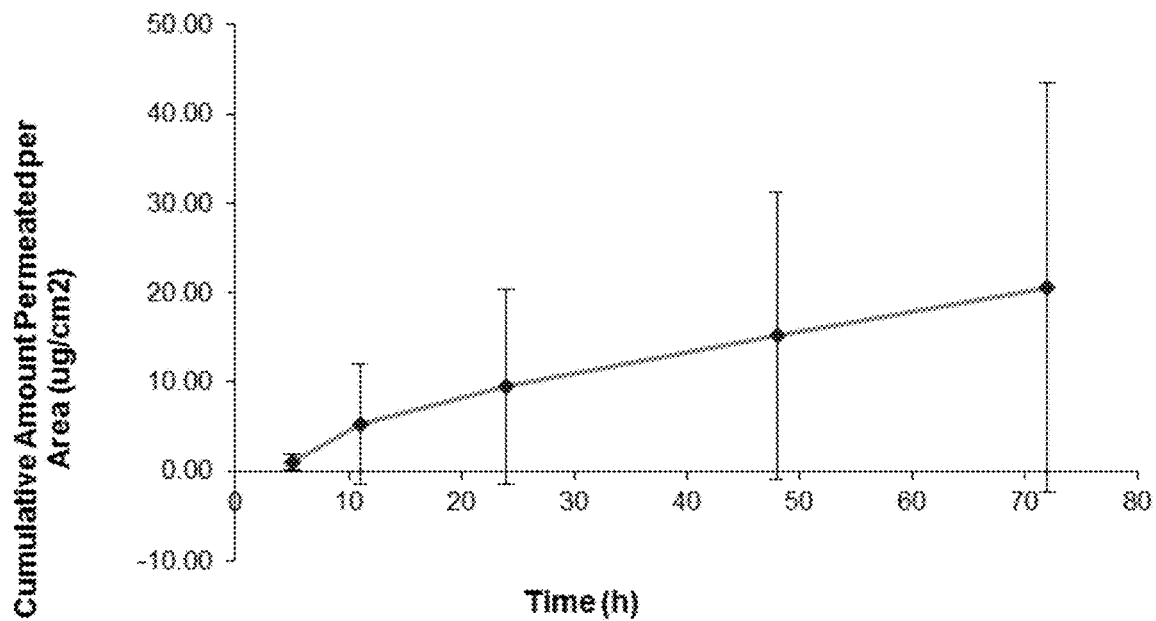
FIG. 3. Graph of cholecalciferol permeation from formulations with adhesive and isosorbide dimethyl ether as an organic solvent/vitamin D solubilizer; average results, n=3.
Figure 4:
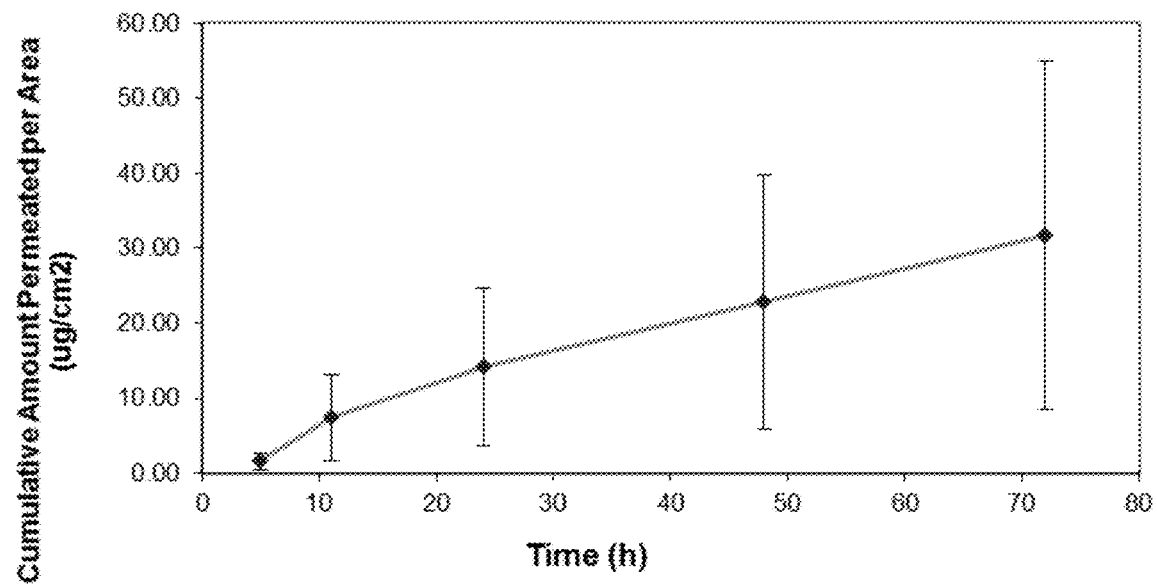
FIG. 4. Graph of cholecalciferol permeation from formulations with adhesive and isopropyl laurate as an organic solvent/vitamin D solubilizer; average results, n=3.

Franz cell permeation of vitamin $D_3$ was then performed to evaluate various formulations that included adhesives (Patch #13 and Patch #14). The results were analyzed and the data is shown in FIGS. 3 and 4.

Patch#13 Lot#FNEK-20150724-1, IDE

| Ingredients: | Quantity (g) |
|---|---|
| Cholecalciferol | 0.2 |
| Labrafac Lipophile WL1349 (oil) | 0.6 |
| Isosorbide dimethyl ether | 0.3 |
| DURO-TAK 87-6908 (PIB) | 9.0 |
| Total | 10.1 |

Patch#14 Lot#FNEK-20150724-2, IPL

| Ingredients: | Quantity (g) |
|---|---|
| Cholecalciferol | 0.2 |
| Labrafac Lipophile WL1349 (oil) | 0.6 |
| Isopropyl laurate | 0.3 |
| DURO-TAK 87-6908 (PIB) | 9.0 |
| Total | 10.1 |

Procedure for Preparation of Patch #13 and Patch #14:

Vitamin $D_3$ (cholecalciferol) was weighed and added to a pre-weighed quantity of labrafac lipophile WL1349 (caprylic/capric triglyceride oil mixture) and mixed for about half an hour. The required quantity of isosorbide dimethyl ether (to prepare Patch #13) or isopropyl laurate (to prepare Patch #14) was added to the mixture and mixing was continued until a homogenous blend was obtained, at which point the cholecalciferol was nearly fully solvated. The desired quantity of PIB was added to the mixture and the blend was mixed overnight by tumbling action on a rotor. The mixture was then coated to 15 mil thickness onto a Scotchpak 1022 release liner and placed in a circulating air oven at 55° C. for 15 minutes. The coated release liner was then removed from the oven and was allowed to cool to room temperature (~22° C.). A backing liner (Scotchpak™ 9733 Backing Polyester Film Laminate) was placed on the coated release liner, with the EVA side facing up. The patches were then pressed by a roller to remove air gaps and to provide efficient bonding with the backing, to provide the final transdermal patch.

Figure 5:
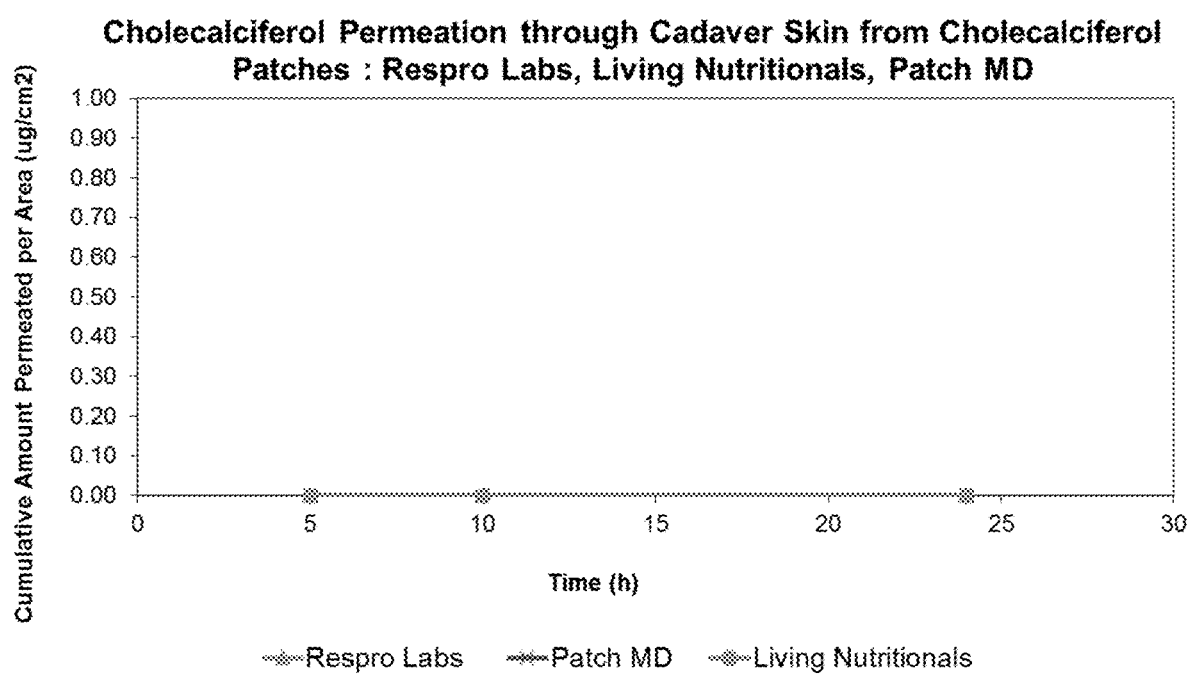
FIG. 5. Graph of cholecalciferol permeation from the commercial products Respro Laboratories Vitamin D Patch (280,000 I.U.), Patch MD Vitamin D3 Topical Patch (5,000 I.U.), and Living Nutritionals Vitamin D3 Sunshine Patch (5,000 I.U.), showing that none of the three commercial patches delivered vitamin D transdermally via Franz Cell evaluations. The data points of all three sets of samples reside on the baseline.

Finally, given the successful transdermal delivery of vitamin D via the formulations of Patch #13 and Patch #14, commercially available patches were then evaluated for their transdermal delivery of vitamin D as determined by Franz Cell analysis. Using the same methods described above, the commercial products Respro Laboratories Vitamin D Patch (280,000 I.U.), Patch MD Vitamin D3 Topical Patch (5,000 I.U.), and Living Nutritionals Vitamin D3 Sunshine Patch (5,000 I.U.) were evaluated. As shown in FIG. 5, while each of these products contain at least 5,000 I.U. of vitamin $D_3$, none of them actually transdermally delivered the vitamin $D_3$ through the cadaver skill in the Franz Cell analysis. Furthermore, only the Respro Laboratories Vitamin D Patch (280,000 I.U.) even released any detectable amounts of vitamin $D_3$ when the experiments were run without cadaver skin, although the Respro Laboratories Vitamin D Patch release less vitamin $D_3$ than Patch #13 and Patch #14.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A transdermal patch for the transdermal administration of cholecalciferol comprising:
    (a) a backing layer that serves as the outer surface of the patch during use;
    (b) an adhesive drug reservoir layer for affixing the patch to human skin; and
    (c) a release liner, which upon removal exposes the adhesive drug reservoir layer;
    wherein the adhesive drug reservoir layer consists of about 1 to about 10 wt % cholecalciferol, a polymeric adhesive, an organic solvent, and a permeation enhancer; the adhesive drug reservoir layer comprises about 1-15 wt. % organic solvent; and the organic solvent comprises isosorbide dimethyl ether or isopropyl laurate.

2. The transdermal patch of claim 1 wherein the adhesive is a polyisobutylene adhesive, a silicone adhesive; or an acrylate adhesive.

3. The transdermal patch of claim 1 wherein the adhesive drug reservoir layer comprises about 60-90 wt. % polymeric adhesive, and the adhesive drug reservoir layer comprises about 1-15 wt. % permeation enhancer.

4. The transdermal patch of claim 1 wherein the adhesive is an acrylate or polyisobutylene adhesive, the organic solvent comprises a triglyceride, and the permeation enhancer is transcutol.

5. The transdermal patch of claim 1 wherein the adhesive drug reservoir layer does not contain water.

6. The transdermal patch of claim 1 wherein the surface area of the adhesive drug reservoir layer of the patch is about 30 cm$^2$ to about 50 cm$^2$.

7. The transdermal patch of claim 6 wherein the patch is formulated to deliver greater than 2,000 µg of cholecalciferol through 40 cm$^2$ of intact unbroken living skin in within 5 hours.

8. The transdermal patch of claim 6 wherein the patch is formulated to deliver greater than 20,000 µg of cholecalciferol through 40 cm$^2$ of intact unbroken living skin in within 24 hours.

9. The transdermal patch of claim 6 wherein the patch is formulated to contain about 4,000-5,000 I.U. of cholecalciferol.

10. A transdermal patch for the transdermal administration of cholecalciferol consisting of:
    (a) a backing layer that serves as the outer surface of the patch during use;
    (b) an adhesive drug reservoir layer for affixing the patch to human skin; and
    (c) a release liner, which upon removal exposes the adhesive drug reservoir layer;
    wherein the adhesive drug reservoir layer consists of 1-10 wt. % of cholecalciferol, 60-90 wt. % of a polymeric adhesive, 1-15 wt. % of an organic solvent, and 1-15 wt. % of transcutol; and
    wherein the organic solvent comprises isosorbide dimethyl ether or isopropyl laurate.

11. The transdermal patch of claim 10 wherein the adhesive drug reservoir layer consists of 3 wt. % of cholecalciferol, 80-85 wt. % of a polymeric adhesive, the organic solvent, and 5-10 wt. % of transcutol.

12. A method for the transdermal delivery of vitamin D comprising removing the release liner of the transdermal patch of claim 10 and applying the transdermal patch to intact unbroken living skin of a human subject, wherein the transdermal patch delivers greater than 0.75 µg/cm$^2$ of cholecalciferol to the subject within 5 hours.

13. The method of claim 12 wherein the transdermal patch is applied to a subject having a 25-hydroxyvitamin D$_3$ (calcifediol) blood serum level of less than 30 ng/mL.

14. The method of claim 13 wherein the transdermal patch is applied to a subject having a 25-hydroxyvitamin D$_3$ (calcifediol) blood serum level of about 1 ng/mL to about 25 ng/mL.

15. The method of claim 14 wherein the 25-hydroxyvitamin D$_3$ (calcifediol) blood serum level of the subject increases to greater than 30 ng/mL within 5 hours.

16. The method of claim 12 wherein the transdermal patch is applied to the subject once per day for at least 5 days.

17. The method of claim 15 wherein the human subject has a 25-hydroxyvitamin D$_3$ (calcifediol) blood serum level of less than 20 ng/mL.

18. The method of claim 17 wherein the human subject has cystic fibrosis, is older than 65 years of age, or has undergone bariatric surgery.

19. A method of increasing the 25-hydroxyvitamin D$_3$ (calcifediol) blood serum level of a human subject that has a vitamin D malabsorption condition comprising removing the release liner of the transdermal patch of claim 1 and applying the transdermal patch to intact unbroken living skin of the human subject, wherein the 25-hydroxyvitamin D$_3$ (calcifediol) blood serum level of the subject increases to greater than 20 ng/mL within 24 hours.

20. The method of claim 19 wherein the human subject that has a vitamin D malabsorption condition is a subject that has been diagnosed with cystic fibrosis.

21. A transdermal patch for the transdermal administration of cholecalciferol consisting of:
    (a) a backing layer that serves as the outer surface of the patch during use;
    (b) an adhesive drug reservoir layer for affixing the patch to human skin; and
    (c) a release liner, which upon removal exposes the adhesive drug reservoir layer;
    wherein the adhesive drug reservoir layer consists of 1-10 wt. % of cholecalciferol, 80-85 wt. % of a polymeric adhesive, 1-15 wt. % of an organic solvent, and 1-15 wt. % of transcutol;
    wherein the organic solvent comprises isosorbide dimethyl ether or isopropyl laurate; and
    wherein the patch is formulated to deliver greater than 2,000 µg of cholecalciferol through 40 cm$^2$ of intact unbroken skin in within 5 hours; and wherein the organic solvent comprises isosorbide dimethyl ether or isopropyl laurate.

* * * * *